United States Patent [19]

Koppel et al.

[11] Patent Number: 4,552,895
[45] Date of Patent: Nov. 12, 1985

[54] FURO[3,2-B]FURAN-2-(3H)-ONES

[75] Inventors: Gary A. Koppel; Russell L. Barton, both of Indianapolis; Stephen L. Briggs, Clayton, all of Ind.

[73] Assignee: Eli Lilly and Company, Indianapolis, Ind.

[21] Appl. No.: 475,272

[22] Filed: Mar. 14, 1983

[51] Int. Cl.$^4$ .................. C07D 307/93; A61K 31/365
[52] U.S. Cl. ...................................... 514/470; 549/306
[58] Field of Search ................ 549/306; 424/280, 279; 514/470

[56] References Cited

U.S. PATENT DOCUMENTS

| | | | |
|---|---|---|---|
| 3,734,929 | 5/1973 | Robinson | 260/343.6 |
| 4,208,434 | 6/1980 | Iacobucci et al. | 426/72 |
| 4,231,939 | 11/1980 | Hartzler | 260/343.6 |
| 4,329,290 | 5/1982 | Sawyer et al. | 549/316 |
| 4,408,061 | 10/1983 | Salzburg et al. | 549/464 |

FOREIGN PATENT DOCUMENTS 86554  8/1983  European Pat. Off. .
2109382  6/1982  United Kingdom .

OTHER PUBLICATIONS

Imai in Chemical Abstracts, 95:90621s.
Shrihatti et al., "Preparation & Properties of 3-Methyl & 2,3-Dimethyl Ethers of Ascorbic Acid", *Ind. J. Chem.* Sect. B, 15B(9), 861 (1977).
*Canadian Journal of Chemistry*, 43, 450 (1965).
*Experientia*, 24 (4), 326 (1968) as abstracted in Chemical Abstracts, 68:111383a.
*Acta Cryst.*, B. 32, 1665 (1976).
*J. Am. Chem. Soc.*, 104, 4497 (1982).
*Acta. Chem. Scand.*, B. 33, 503 (1979).
*Chemistry and Industry*, 89 (1965).

Primary Examiner—Jane T. Fan
Attorney, Agent, or Firm—Charles W. Ashbrook; Arthur R. Whale

[57] ABSTRACT

The invention provides for certain compounds derived from ascorbic acid and their formulations which are useful in inhibiting angiogenesis in mammals.

20 Claims, No Drawings

FURO[3,2-B]FURAN-2-(3H)-ONES

BACKGROUND OF THE INVENTION

Tumor angiogenesis is the formation of capillary sprouts induced by a group of tumor cells. These sprouts eventually develop into a microcirculatory network within the tumor mass. There are two principle types of tumor angiogenesis in terms of the events which follow implantations of metastatic seedlings on surfaces and in organs.

The first or primary angiogenesis is the initial vascularization of the mass of multiplying tumor cells and is regarded as an essential prerequisite for the survival and further growth of a metastatic deposit.

The second is the continuing or secondary angiogenesis and is the phenomenon which occurs in waves at the periphery of a growing tumor mass. This secondary angiogenesis is essential for the accretion of new microcirculatory territories into the service of the expanding and infiltrating tumor.

Other types of angiogenesis not associated with tumor formation or growth are found in the development of retinopathy, psoriasis and rheumatoid arthritis (pannus formation). Several different research groups have purified angiogenesis factors from different disease states.

It is apparent that a chemical which would inhibit angiogenesis, eigher by competitively inhibiting an angiogenesis factor or by some other mechanism, would have an adverse effect upon the growth of tumors, on the development of retinopathy or rheumatoid arthritis, or on the development of the psoriatic lesion. It is an object of this invention to provide a group of compounds which inhibit angiogenesis wherever found.

SUMMARY OF THE INVENTION

This invention relates to compositions of matter defined by the general structural Formula I

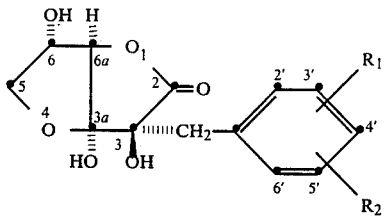

wherein each $R_1$ and $R_2$ is independently hydrogen, hydroxy, $C_1-C_3$ alkoxy, $C_1-C_3$ alkyl, halo, trifluoromethyl, nitro, or amino, with the limitation that when one of $R_1$ and $R_2$ is hydrogen, the other of $R_1$ and $R_2$ may not be hydrogen or hydroxy.

A further aspect of this invention provides a method of inhibiting angiogenesis which comprises administering to a mammal in need of treatment an angiogenesis inhibiting amount of a compound of the Formula I.

An additional embodiment of this invention is a pharmaceutical formulation comprising a compound of Formula I in combination with a suitable pharmaceutical carrier, diluent, or excipient therefor. The formulations provided by this invention are particularly useful in treating mammals for which the treatment of angiogenesis is indicated.

DETAILED DESCRIPTION AND PREFERRED EMBODIMENT

The term "$C_1-C_3$ alkyl" refers to methyl, ethyl, n-propyl, an isopropyl. The term "$C_1-C_3$ alkoxy" refers to methoxy, ethoxy, n-propoxy, and isopropoxy. The term "halo" refers to fluoro, chloro, bromo and iodo.

The preferred compounds of this invention are those compounds of Formula I wherein $R_2$ is hydrogen. Particularly preferred mono-substituted benzyl derivatives are those wherein $R_1$ is halo, trifluoromethyl, or methyl. The preferred mono-substituted compounds are those wherein $R_1$ is in the 3'- and especially the 4'-position.

The compounds of Formula I are chemically known as [3R-(3aα,6α,6aα)]-tetrahydro-3,3a,6-trihydroxy-3-[($R_1$,$R_2$-substituted phenyl)methyl]furo[3,2-b]furan-2-(3H)-ones.

The compounds of this invention are prepared by reacting L-ascorbic acid (Formula II)

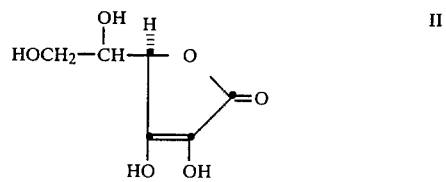

with a substituted benzyl halide of Formula III

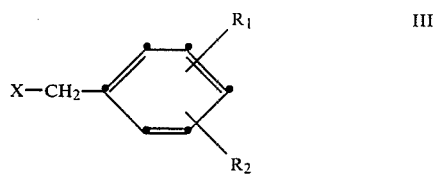

wherein $R_1$ and $R_2$ are the same as described previously and X is chloro, bromo, or iodo.

The reaction is carried out by reacting approximately equal molar equivalents of compounds II and III in a non-reactive solvent, such as dioxane, N,N-dimethylformamide, acetonitrile, or preferably dimethylsulfoxide (DMSO). Additionally, one molar equivalent of a suitable acid scavenger is employed such as an alkali metal alkoxide, preferably sodium methoxide. The reaction is carried out at temperatures from about 20° C. to the reflux temperature of the reaction mixture, preferably at temperatures of about 50°–70° C. At these preferred temperatures, the reaction is usually complete within 24 hours.

The compounds of this invention may be administered by various routes including the oral, rectal, transdermal, subcutaneous, intravenous, intramuscular, or intranasal routes, being usually employed in the form of a pharmaceutical composition, although it is a special feature of these compounds that they are effective following oral administration. Such compositions are prepared in a manner well known in the pharmaceutical art and comprise at least one active compound. Accordingly the invention includes a pharmaceutical composition comprising as active ingredient a compound of Formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

Preferably the compositions are formulated in a unit dosage form, each dosage containing from 5 to 500 mg., more usually 25 to 300 mg., of the active ingredient. The term "unit dosage form" refers to physically discrete units suitable as unitary dosages for human subjects and animals, each unit containing a predetermined quantity of active material calculated to produce the desired therapeutic effect, in association with the required pharmaceutical carrier.

The active compounds are effective over a wide dosage range and for example dosages per day will normally fall within the range of about 0.5 to 300 mg./kg. of mammalian body weight. In the treatment of adult humans, the range of from about 1 to 50 mg./kg., in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

In an effort to more fully illustrate the operation of this invention, the following detailed Examples are provided. The examples are illustrative only and are not intended to limit the scope of the invention in any way.

EXAMPLE 1

[3R-(3aα,6α,6aα)]-tetrahydro-3,3a,6-trihydroxy-3-[(4-fluorophenyl)methyl]furo[3,2-b]furan-2(3H)-one To a solution of 26.4 g. (150 mmoles) of L-ascorbic acid and 8.2 g. (152 mmoles) of sodium methoxide in 125 ml. of dimethylsulfoxide at 65°–70° C. was added over a 15 minute period a solution of 36.9 g. (156 mmoles) of 4-fluorobenzyl iodide in 75 ml. of dimethylsulfoxide. After stirring at about 65° C. for one hour, the temperature was reduced to about 50° C. and the reaction was stirred for an additional 20 hours. A saturated sodium chloride solution (500 ml.) was added to the reaction mixture and the solution was extracted with 750 ml. of ethyl acetate. The ethyl acetate was washed with 500 ml. of a saturated sodium chloride solution followed by washing with 500 ml. of a 1N sodium thiosulfate solution and an additional 500 ml. of a saturated sodium chloride solution. The ethyl acetate solution was dried over magnesium sulfate and treated with decolorizing carbon overnight. The ethyl acetate solution was filtered and the filtrate was concentrated in vacuo leaving a brown syrup. The syrup was dissolved in a minimum of hot ethyl acetate and a large excess of toluene was added. After 8 days, the resulting crystals were harvested by filtration and were recrystallized an additional three times from ethyl acetate/toluene to give 4.7 g. of the title product as a white crystalline solid, m.p. about 131°–133° C.

Analysis: $C_{13}H_{13}FO_6$; Calculated: C, 54.93; H, 4.61; F, 6.68; Found: C, 54.73; H, 4.57; F, 6.41.

EXAMPLES 2–13

Following the procedure of Example 1, the following compounds were prepared using the appropriate substituted benzyl halide.

TABLE I

| Compound of Formula I | | | | Elemental Analysis (%) | | | | | |
|---|---|---|---|---|---|---|---|---|---|
| Example | | | | Calculated | | | Found | | |
| No. | $R_1,R_2$ | % yield | m.p. | C | H | Other | C | H | Other |
| 2 | 3'-Br | 12% | 137–139° C. | 45.24 | 3.80 | Br, 23.15 | 45.08 | 4.00 | Br, 23.30 |
| 3 | 3'-Cl | 11% | 129–131° C. | 51.93 | 4.36 | Cl, 11.79 | 51.99 | 4.25 | Cl, 11.91 |
| 4 | 2'-Cl | 17% | 160–161° C. | 51.93 | 4.36 | Cl, 11.79 | 52.09 | 4.68 | Cl, 11.64 |
| 5 | 4'-Cl | 18% | 148–149° C. | 51.93 | 4.36 | Cl, 11.79 | 52.26 | 4.46 | Cl, 11.97 |
| 6 | 2'-F | 22% | 165–167° C. | 54.93 | 4.61 | F, 6.68 | 54.74 | 4.54 | F, 6.62 |
| 7 | 3'-F | 11% | 154–156° C. | 54.93 | 4.61 | F, 6.68 | 54.89 | 4.72 | F, 6.46 |
| 8 | 4'-CF$_3$ | 14% | 150–151° C. | 50.31 | 3.92 | F, 17.05 | 50.47 | 3.90 | F, 16.78 |
| 9 | 3'-CH$_3$ | 8% | 141–143° C. | 60.00 | 5.75 | | 60.23 | 5.89 | |
| 10 | 2'-CH$_3$ | 10% | 132–134° C. | 60.00 | 5.75 | | 59.97 | 5.68 | |
| 11 | 4'-CH$_3$ | 12% | 134–136° C. | 60.00 | 5.75 | | 60.25 | 5.67 | |
| 12 | 2',5'-(CH$_3$)$_2$ | 13% | 174–176° C. | 61.22 | 6.17 | | 61.44 | 6.02 | |
| 13 | 4'-NO$_2$ | 3% | 131–133° C. | 50.17 | 4.21 | N, 4.53 | 50.40 | 4.29 | N, 4.69 |

The following formulation examples employ as active compounds any of the pharmaceutical compounds of the invention.

EXAMPLE 14

Hard gelatin capsules are prepared using the following ingredients:

| | Quantity (mg./capsule) |
|---|---|
| Active compound | 250 |
| Starch dried | 200 |

| | Quantity (mg./capsule) |
|---|---|
| Magnesium stearate | 10 |

The above ingredients are mixed and filled into hard gelatin capsules in 460 mg. quantities.

EXAMPLE 15

A tablet formula is prepared using the ingredients below:

| | Quantity (mg./tablet) |
|---|---|
| Active compound | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 16

An aerosol solution is prepared containing the following components:

| | Weight % |
|---|---|
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

EXAMPLE 17

Tablets each containing 60 mg. of active ingredient are made up as follows:

| | |
|---|---|
| Active ingredient | 60 mg. |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The soluion of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 18

Capsules each containing 80 mg of medicament are made as follows:

| | |
|---|---|
| Active ingredient | 80 mg. |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 19

Suppositories each containing 225 mg. of active ingredient are made as follows:

| | |
|---|---|
| Active ingredient | 225 mg. |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to cool.

EXAMPLE 20

Suspensions each containing 50 mg. of medicament per 5 ml. dose are made as follows:

| | |
|---|---|
| Active ingredient | 50 mg. |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

As previously stated, the compounds of this invention inhibit angiogenesis factor's action of promoting the development of blood vessels (as part of the growth process) by tumors, by which mechanism the tumor is able to form an adequate blood supply system. One method of demonstrating such angiogenesis factor inhibitory action in vivo is by the following test procedure.

Lysosomal-mitochondrial pellets containing angiogenesis factor are prepared from 3683 Morris hepatoma. The pellet is diluted with 7-8 ml. of 15% ficoll. At this dilution, 8-10 serpentine vessels are usually produced per 0.2 cc. injection as described below for the control group. The dilution may be adjusted upward or downward to bring the number of serpentine vessels induced within the 8-10 range so as to provide comparable concentrations of angiogenesis factor per lysosomal-mitochondrial preparation.

Next, 15 SPF/ND4 female mice weighing 20-22 g. are shaved on the left side and then divided into three groupss of five each. One group (drug group) is injected subcutaneously and laterally with 0.2 cc. of the lysosomal-mitochondrial preparation diluted with 15% ficoll. This group of mice is then dosed individually by the intraperitoneal route with 0.5 cc. of a solution or suspension in a standard vehicle containing the compound under test, usually at an initial dose level of 300 mg./kg. If this dose level is toxic, two-fold dilutions are made until all mice survive a single dose. The second group of mice (control group) is injected subcutaneously and laterally with 0.2 cc. of the lysosomal-mitochondrial suspension diluted with ficoll and dosed intraperitoneally with 0.5 cc. of the vehicle alone. The third group of mice (negative control) is injected with the ficoll solution only (without the lysosomal-mitochondrial pellet) without treatment with compound or vehicle. The mice are sacrificed after 24 hours. Each mouse is placed on its side on a dissecting board with the shaved side up. Starting at the flank, the skin is cut straight to the back of the animal. A similar cut is made behind the front leg. The skin is then cut along the back making a flap of about one inch by two inches. The skin is carefully separated from the connective tissue by using forceps and a scalpel. The skin flap is then laid back exposing the lysosomal-mitochondrial implant which is attached to the skin. The skin flap is gently flattened out and with the use of a binocular dissecting scope, serpentine vessels are observed around the lysosomal-mitochondrial implant and their number counted. All observations of the number of serpentine vessels are made at the same power of the microscope (1×). The average number of serpentine vessels for each group is calculated. The percent inhibition is then calculated according to the following equation.

$$\% \text{ inhibition} = \left[1 - \frac{\overline{sv} \text{ (drug group)}}{\overline{sv} \text{ (control group)}}\right] \times 100$$

where $\overline{sv}$ = averge number of serpentine vessels.

If the negative control group described above has any serpentine vessels, the test is invalid due to contamination of the ficoll solution.

Table II which follows gives the results of these tests.

TABLE II

Tumor Angiogenesis Inhibition of Compounds of Formula I*

| Compound of Example No. | % inhibition |
|---|---|
| 1 | 62% |
| 2 | 45% |
| 3 | 55% |
| 4 | 38% |
| 5 | 52% |
| 6 | 33% |
| 7 | 57% |
| 8 | 55% |
| 9 | 48% |
| 10 | 48% |
| 11 | 62% |
| 12 | 58% |

*All compounds tested i.p. at a dose of 25 mg./kg.

A second laboratory test has been employed to demonstrate the activity of compounds according to Formula I above as inhibitors of angiogenesis. This test method is a collagen arthritis assay carried out as follows.

Type II collagen is isolated from bovine articular cartilage by the method of Strawich and Nimni [*Biochemistry*, 10, 3905 (1971)]. The collagen is dissolved in 0.1M acetic acid and stored at −20° C. Type II collagen solution is diluted to 2 mg./ml. concentration and emulsified thoroughly with an equal volume of incomplete Freund's adjuvant (ICFA). The emulsion containing approximately 0.5 mg. of collagen is injected intradermally on day 0 to groups of 6 inbred Lewis male rats (Charles River Breeders; 170–200 g.) at various sites in the dorsal area. The hindpaw volumes of each rat are measured and recorded three times a week throughout the test period to assess the inflammatory reaction. The test group animals receive compounds under test as suspensions in carboxymethylcellulose vehicle, by oral gavage, 5 days per week (Monday–Friday), beginning on day 1. Control animals receive vehicle without a test compound. At the end of the test (day 28 or 30), the blood of these animals is drawn by cardiac puncture and the serum anti-type II collagen antibody levels are estimated by passive hemagglutination technique, using glutaraldehyde treated sheep red cells, to which type II collagen is conjugated [Avrameas et al., *Immunochemistry*, 6, 67 (1969); Andriopoulos et al., *Arth. Rheum.*, 19, 613 (1976)]. The cellular response or delayed-type hypersensitivity response to type II collagen is measured by the radiometric ear index assay [Kostiala, *Immunology*, 33, 561 (1977)]. In certain experiments, the bone damage occurring because of immunization with type II collagen and the effects of drugs are determined from the radiographs of the hindpaws of two or three representative animals from each group. Injections of ICFA without collagen II were employed to some rats as a negative control; these rats received only carbomethoxycellulose vehicle during the test.

The results of testing certain compounds of Formula I in the collagen-induced arthritis system are summarized in Table III. The % inhibition is calculated according to the following formula:

$$\% \text{ inhibition} = \left[1 - \frac{Vt - Vv}{Vc - Vv}\right] \times 100$$

where Vt is the hindpaw volume of a compound-treated animal (test group), Vc is the hindpaw volume of a non-compound-treated animal (carbomethoxycellulose vehicle only-the control group), the Vv is the hindpaw volume of a vehicle (carbomethoxycellulose) treated animal which received ICFA with no collagen II (negative control group).

TABLE III

Inhibition of Collagen-Induced Arthritis

| Compound of Example No. | Dose mg./kg.* | % inhibition* |
|---|---|---|
| 1 | 25 | 94% |
| 3 | 15 | 100% |
| 5 | 15 | 81% |
| 7 | 25 | 100% |
| 11 | 15 | 94% |
| 12 | 25 | 23% |

*See text for experimental method.

We claim:

1. A compound of the formula

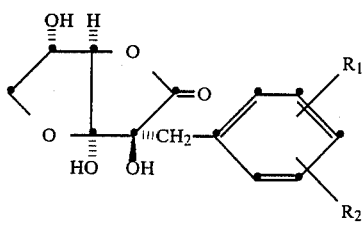

wherein each $R_1$ and $R_2$ is independently hydrogen, hydroxy, $C_1$-$C_3$ alkoxy, $C_1$-$C_3$ alkyl, halo, trifluoromethyl, nitro, or amino, with the limitation that when one of $R_1$ and $R_2$ is hydrogen, the other of $R_1$ and $R_2$ may not be hydrogen or hydroxy.

2. A compound of claim 1 wherein $R_2$ is hydrogen.

3. A compound of claim 2 wherein $R_1$ is in the 3'-position.

4. A compound of claim 2 wherein $R_1$ is in the 4'-position.

5. A compound of claim 2 wherein $R_1$ is halo.

6. A compound of claim 2 wherein $R_1$ is methyl.

7. A compound of claim 2 wherein $R_1$ is trifluoromethyl.

8. The method of inhibiting collagen-induced arthritis which comprises administering to a mammal in need of treatment an effective amount of a compound according to claim 1.

9. The method of claim 8 wherein $R_2$ is hydrogen.

10. The method of claim 9 wherein $R_1$ is in the 3'-position.

11. The method of claim 9 wherein $R_1$ is in the 4'-position.

12. The method of claim 9 wherein $R_1$ is halo.

13. The method of claim 9 wherein $R_1$ is methyl.

14. The method of claim 9 wherein $R_1$ is trifluoromethyl.

15. A pharmaceutical formulation useful for inhibiting collagen-induced arthritis in a mammal which comprises an effective amount of a compound according to claim 1 in combination with suitable pharmaceutical carriers, diluents, or excipients therefor.

16. A formulation according to claim 15 wherein $R_2$ is hydrogen.

17. A formulation according to claim 16 wherein $R_1$ is in the 3'-position.

18. A formulation according to claim 16 wherein $R_1$ is in the 4'-position.

19. A formulation according to claim 16 wherein $R_1$ is halo.

20. A formulation according to claim 16 wherein $R_1$ is methyl.

* * * * *